(12) United States Patent
Jones et al.

(10) Patent No.: US 6,309,406 B1
(45) Date of Patent: Oct. 30, 2001

(54) APPARATUS AND METHOD FOR INDUCING EPILEPTIC SEIZURES IN TEST ANIMALS FOR ANTICONVULSANT DRUG SCREENING

(75) Inventors: Gary L. Jones, Dammeron Valley, UT (US); Robert R. Rainey, Elkhart, IN (US)

(73) Assignee: Hamit-Darwin-Fresh, Inc., Ivins, UT (US)

(*) Notice: Subject to any disclaimer, the term of this patent is extended or adjusted under 35 U.S.C. 154(b) by 0 days.

(21) Appl. No.: 09/448,719

(22) Filed: Nov. 24, 1999

(51) Int. Cl.[7] ...................................................... A61N 1/00
(52) U.S. Cl. ................................................................ 607/2
(58) Field of Search ............................ 607/2, 3, 45, 48, 607/58, 62, 66–76; 600/544, 545, 546

(56) References Cited

U.S. PATENT DOCUMENTS

| | | |
|---|---|---|
| 3,817,254 | 6/1974 | Maurer . |
| 4,121,593 | 10/1978 | Kastrubin et al. . |
| 4,174,706 | 11/1979 | Jankelson et al. . |
| 4,503,863 | 3/1985 | Katims . |

Primary Examiner—Scott M. Getzow
(74) Attorney, Agent, or Firm—TraskBritt

(57) ABSTRACT

A stimulator for electrically inducing a maximal seizure in a test animal for screening candidate anticonvulsant drugs is disclosed. A stimulator according to this invention includes stimulus generation and control circuitry for generating the stimulus, a display for displaying the duration of three phases of the induced seizure, and user input configured to allow the user to control delivery of the stimulus and to record seizure phase transitions to be displayed on the display. The stimulator may also include a foot switch, electrodes, a computer interface and an optional computer. A method of measuring the phases of an electrically induced seizure is disclosed. A method of analyzing the efficacy of a candidate anticonvulsant drug is also disclosed.

21 Claims, 8 Drawing Sheets

APPARATUS AND METHOD FOR INDUCING EPILEPTIC SEIZURES IN TEST ANIMALS FOR ANTICONVULSANT DRUG SCREENING

TECHNICAL FIELD

This invention relates to the field of electrical stimulation. More particularly, this invention relates to an apparatus and method for inducing epileptic seizures in small mammals.

BACKGROUND

Epilepsy is a disorder marked by recurring motor, sensory, or psychic malfunctions which may include unconsciousness or convulsive movements. The International League Against Epilepsy Revised Classification of Epileptic Seizures (1981) categorized the spectrum of epileptic seizures from partial to generalized. A form of generalized convulsive seizure is the "grand mal" or generalized "tonic-clonic" seizure. Such seizures usually involve a relatively short, 10–30 second, tonic phase noted by flexion and extension of muscles, but no shaking followed by a longer, 15–60 second, clonic-tonic phase manifesting as rhythmic muscle group shaking. Hereinafter the terms "seizure", "grand mal seizure", "epileptic seizure", and "maximal seizure" are used interchangeably and synonymously with the generalized tonic-clonic seizure as previously outlined herein.

Many drugs are used to treat epilepsy, generally referred to as anticonvulsants. The older and well tested anticonvulsants include phenobarbital and primidone, neither of which are in common use today because of side effects and phenytoin (which goes by the brand name DILANTIN™) and cabamazepine (TEGRETOL™) and valproate (DEPAKOTE™, EPILIM™).

Newer anticonvulsants, such as felbamate (FELBATOL™), gabapentin (NEURONTIN™), lamotrigine (LAMICTAL™), tiagabine (GABITRIL™) and topiramate (TOPAMAX™), are technically marketed in the United States as "adjunctive anticonvulsants" because they are used in combination with older anticonvulsants. Such newer anticonvulsants may prove more useful in treating epilepsy than older drugs, but more testing and research will be necessary. The search for more effective anticonvulsant drugs continues.

Research into the effectiveness of new anticonvulsant drugs typically involves screening candidate drugs in small mammals such as mice or rats (hereinafter "test animal") prior to clinical evaluation on humans. In order to gauge the efficacy of a candidate drug, its anticonvulsive effect is observed in a test animal that may have been electrically induced to have a grand mal seizure. An electrical stimulator (hereinafter simply referred to as a "stimulator") is used to generate a sufficient stimulus to induce a grand mal seizure in a test animal. The use of electrically-induced seizures in test animals for studying the effects of anticonvulsant treatments, drug therapy and other procedures dates back at least as early as 1937.

The effects of various levels of electrical stimulation in test animals, particularly rats, is disclosed in Lowell A. Woodbury and Virginia D. Davenport, *Design and Use of a New Electroshock Seizure Apparatus, and analysis of Factors Altering Seizure Threshold and Pattern*, Arch. Int. Pharmacodyn., Vol. XCII, No. 1, 1952, the entire disclosure of which is herein incorporated by this reference and is hereinafter referred to as Woodbury and Davenport.

A maximal seizure in a test animal, as disclosed in Woodbury and Davenport, may be broken down into distinct phases. The first phase is a hindleg flexor component of the tonic phase, wherein the test animal flexes (contracts or pulls inward) its hindlegs. This first phase lasts approximately four seconds for a rat. The second phase is a hindleg extensor component of the tonic phase, wherein the test animal extends its hindlegs. This second phase lasts for approximately six seconds for a rat. The third phase includes intermittent, whole-body clonus (clonic phase), wherein the test animal's movements include rapidly alternating muscular contraction and relaxation. This third phase lasts for approximately five seconds in a rat. The fourth and final phase is muscular relaxation followed by seizure termination.

Candidate anticonvulsant drugs are typically selected based on their ability to shorten or eliminate any of the first three phases of a grand mal seizure in a test animal. For this reason, it is particularly important to measure the first three phases of the seizure to determine to what extent a given anticonvulsant drug reduces the severity of a seizure.

Woodbury and Davenport disclose a conventional apparatus for generating an stimulus suitable for inducing seizures in test animals. The Woodbury and Davenport stimulator delivers a 60 Hertz sinusoidal electrical stimulus. The Woodbury and Davenport stimulator includes a variable transformer rated at 2000 volts rms (root mean square) and provides five current ranges, 10, 25, 50, 100 and 500 milliamperes. Current ranges are selected by changing series resistance. The current is preset to the desired value by setting the primary voltage using the variable supply transformer and a voltmeter calibrated in terms of the current delivered. The voltmeter is calibrated using a 500 ohm dummy load in series with an ammeter placed across the output terminals. A switch is manually closed and the variable transformer turned up until the current through the dummy load has a given value. A potentiometer is adjusted until the ammeter reads the given value. The ammeter is thus calibrated and may be read directly. The resistance of the test animal is assumed to be 500 ohms.

The Woodbury and Davenport stimulator also discloses a conventional timing circuit including a capacitor charged from a regulated power supply which is discharged through a series resistor using a relay. The length of time the relay is closed may be varied by varying the series resistance.

Noticeably lacking in the Woodbury and Davenport stimulator is any kind of timing mechanism for recording the seizure phases (e.g., hindleg flexor tonic, hindleg extensor tonic, whole-body clonic, etc.) which is critical to evaluating the efficacy of an experimental anticonvulsant drug. The use of solid state components in a stimulator is also preferred because of superior reliability, and is clearly lacking in the vintage Woodbury and Davenport stimulator.

Another apparatus currently used in research laboratories is the Hugo Sachs (Freiburg, Germany), Type 221, stimulator. However, the Hugo Sachs device also does not appear to have timing mechanisms for recording the distinct seizure phases of test animals during anticonvulsant drug screening.

None of the above aforementioned devices and publications appears to disclose an apparatus capable of delivering a stimulus with a wide range of current ranges with built-in timers for recording phases of the induced seizures. It is desirable to have such a stimulator because the efficacy of a candidate anticonvulsant drug is in part measured by its effect on reducing the duration of a given seizure, which, in turn, has distinct phases. Additionally, none of the prior art devices appear to have a foot switch which allows the user to change the operational state of the stimulator and mark timing events while leaving both hands free to secure the electrodes on the test animal and position the animal until the stimulus is delivered. Thus, a need in the art exists for a stimulator and methods for inducing epileptic seizures and measuring the phases of the induced seizures in test animals for screening anticonvulsant drugs.

BRIEF SUMMARY OF THE INVENTION

An embodiment of a stimulator in accordance with the invention includes stimulus generation and control circuitry for providing an electrical stimulus sufficient to induce an epileptic seizure in a laboratory test animal, a display coupled to the stimulus generation and control circuitry for displaying three phases of the epileptic seizure, and user input coupled to the stimulus generation and control circuitry configured to allow the user to control delivery of said electrical stimulus and enter seizure phase transitions.

Another embodiment of a stimulator configured for inducing a maximal seizure in test animals according to this invention includes a digital controller for controlling operations of the stimulator, a stimulus generator coupled to the digital controller for providing a stimulus sufficient to induce a maximal epileptic seizure in a laboratory test animal, and a display coupled to the digital controller configured for displaying operational status of the stimulator and seizure phase duration.

The invention also includes a method of operating such a stimulator. The invention includes a method of measuring the phases of an electrically induced seizure in a test animal. Further, the invention includes a method of analyzing the efficacy of a candidate anticonvulsant drug by measuring the phases of an electrically induced seizure in a test animal.

These embodiments, methods and attendant advantages of the invention will be readily understood by reading the following detailed description in conjunction with the accompanying figures of the drawings.

BRIEF DESCRIPTION OF THE DRAWINGS

In the drawings, which illustrate what is currently regarded as the best mode for carrying out the invention, and in which like reference numerals refer to like parts in different views or embodiments.

BEST MODE OF THE INVENTION

The following detailed description discloses various embodiments of a stimulator suitable for electrically inducing seizures in test animals for the purpose of measuring the efficacy of candidate anticonvulsant drugs. The following detailed description also discloses methods of operating the inventive stimulator and methods of screening candidate anticonvulsant drugs using the inventive stimulator. The term "stimulus" is used herein to mean an electrical signal configured to induce an epileptic seizure in a test animal.

Figure 1:
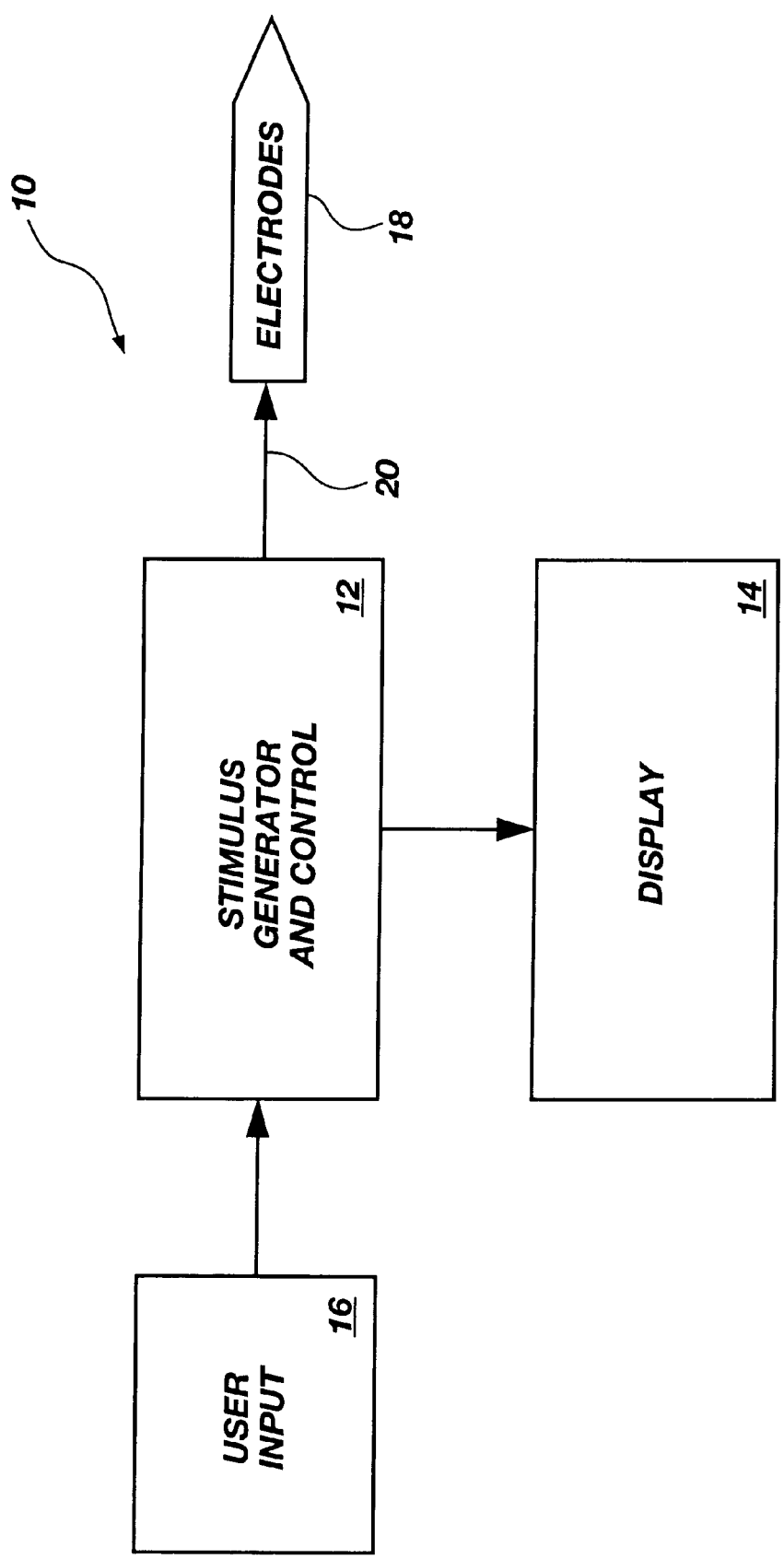
FIG. 1 is a block diagram of a stimulator according to this invention.

FIG. 1 is a block diagram of a stimulator 10 according to the invention. The stimulator 10 includes a stimulus generator and control block 12 for generating an electrical stimulus sufficient to induce a maximal seizure in a test animal. The test animals may be mice, rats or other small rodents commonly known to, and used by, those of skill in the art. The stimulus generator and control block 12 is coupled to a display 14. Display 14 may be, for example, a cathode ray tube, LCD, gas-plasma display, field effect display, printer, or any other type of visual display for conveying numerical or graphical information to users or observers. The numerical or graphical information, hereinafter "display information", may include individual timers for various phases of a seizure being induced and monitored in a test animal. Display information may include current settings and/or activation time of stimulus. Display 14 may be integrated into the stimulator 10 or may be a separate component such as a monitor coupled to the stimulator 10 by a video cable or other means well known to a person of skill in the art. Display 14 may be a combination of individual displays grouped together, or apart, for displaying numerical or graphical information.

The stimulator 10 also includes a user input 16. The user input 16 may include user controls (not shown) physically located on a chassis containing the stimulus generator and control block 12 allowing the user to control the operations of the stimulator 10 by setting the current and duration of the stimulus (also referred herein as "activation time"). In what is presently considered the preferred embodiment of the present invention, the user input includes a foot switch configured to allow the user to change the state of operation of the stimulator 10 and enter timing signals corresponding to the transitions in the various phases of an electrically induced seizure. For example, and not by way of limitation, a foot switch may be used to activate the stimulus and thereafter to activate and deactivate timers for recording the duration of seizure phases. Each pressing of the foot switch may turn off a timer and simultaneously activate another timer allowing the user to simply "mark" the transitions between seizure phases.

The stimulator 10 may also include electrodes 18 coupled to the stimulus generator and control block 12. The electrodes 18 may then be coupled to the stimulus generator and control block 12 with a cable or wiring 20. The electrodes 18 may be Spiegel™ type, corneal electrodes, i.e., small segments of a hollow metal sphere with leads soldered to the convex surface, or any other suitable electrode configuration.

Figure 2:
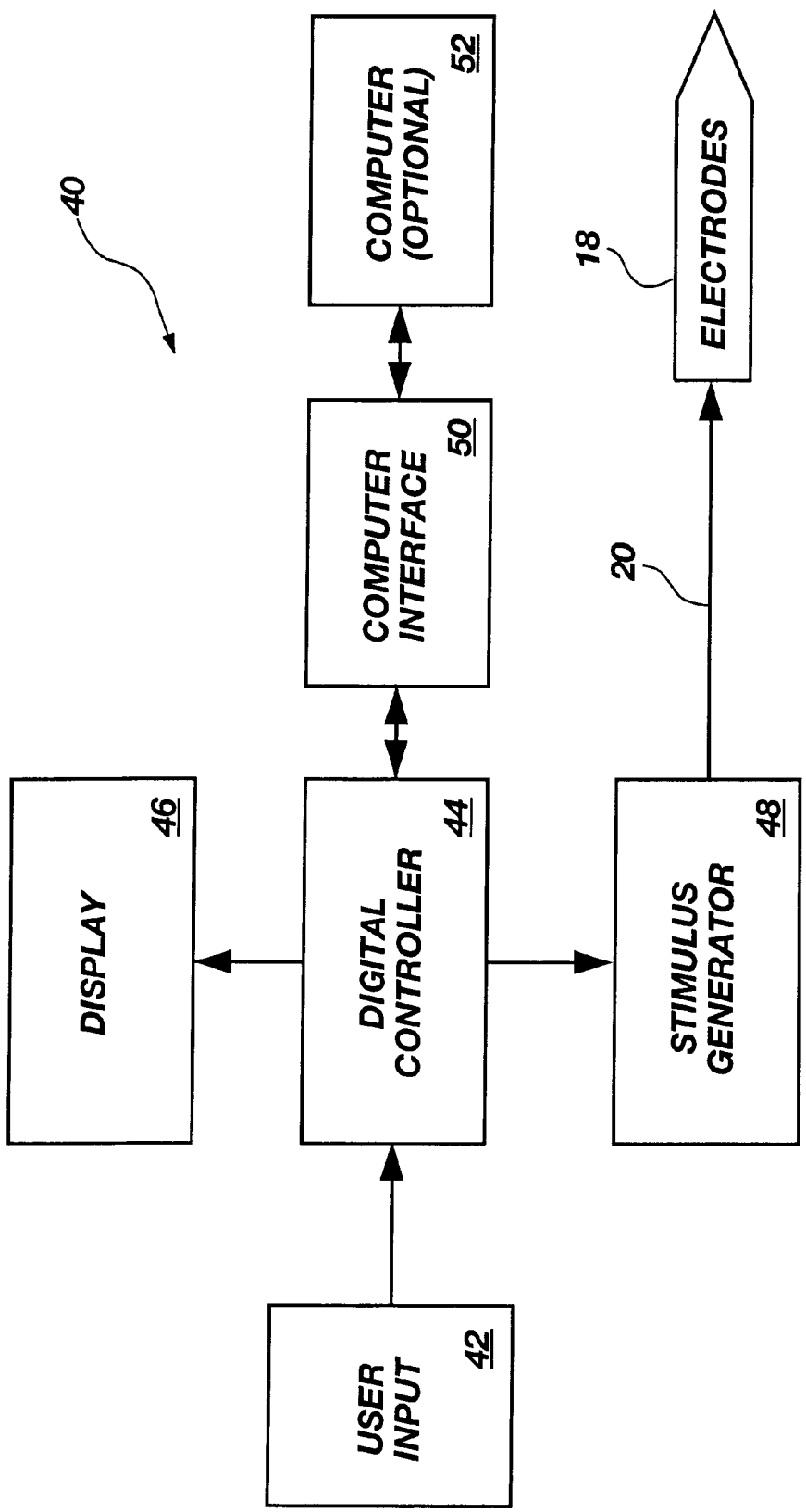
FIG. 2 is a block diagram of another embodiment of a stimulator according to this invention.

FIG. 2 illustrates a block diagram of another embodiment of a stimulator 40 according to the invention. The stimulator 40 includes a user input 42 coupled to a digital controller 44, a display 46 coupled to the digital controller 44, a stimulus generator 48 coupled to the digital controller 44, a computer interface 50 coupled to the digital controller 44, an optional computer 52 coupled to the computer interface 50, and electrodes 18 coupled to the stimulus generator 48.

Digital controller 44 may include a microprocessor, a micro-controller or other programmable logic device for receiving input signals from user input 42 and providing control signals to the stimulus generator 48 and the display 46. Digital controller 44 includes at least three timing circuits (not shown) for measuring seizure phases based on input signals received from user input 42. Digital controller 44 also provides information to, and receives information from, the computer interface 50 when connected to the optional computer 52. The optional computer 52 may be used to program the stimulator 40 and may also be used to store and analyze timing information input by the user via the user input 42 and received by the digital controller 44. Digital controller 44 also provides timing information to be displayed on display 46. One may eliminate the display 46 when the optional computer 52 is included in the stimulator 40, and a computer monitor (not shown) included with the optional computer 52 may be used to present the display information:

Display 46 may be a cathode ray tube, LCD, gas-plasma display, field effect display, printer, or any other type of visual display for conveying display information to users or observers. Display 46 may be integrated into the stimulator 40 or may be a separate component such as a monitor coupled to the stimulator 40 by a video cable or other means well known to a person of skill in the art. Display 46 may be a combination of individual displays grouped together, or apart, for displaying numerical or graphical information. Display 46 may be used to visually display activation time and elapsed time in various phases of a seizure as input by the user with user input 42.

Stimulus generator 48 provides a controlled stimulus according to control signals received from digital controller 44. The stimulus generated by the stimulus generator 48 is a sinusoidal electrical signal with current ranging from about 2 mA rms to about 250 mA rms and preferably in the range from about 4 mA rms to about 200 mA rms. The sinusoidal stimulus generated by the stimulus generator 48 has voltage ranging from about ±180 volts to about ±240 volts, preferably ranging about ±190 volts. Stimulus generator 48 may include a power supply, power amplification circuitry, filter circuitry and other circuitry well known in the art for generating a stimulus as described herein. Computer interface 50 may be any conventional computer interface suitable for communicating data to and from the stimulator 40. The optional computer 52 may be any conventional computer, whether portable or desktop, and may include any computer architecture and operating system as long as it is capable of communicating through the computer interface 50.

User input 42 may include user controls (not shown) which may be physically integrated with the stimulator 40, or remotely coupled to the stimulator 40, for setting the current and activation time of the stimulus. User input 42 preferably includes a foot switch (not shown for clarity) configured to allow a user to change the state of operation of the stimulator 40 and enter timing signals corresponding to the transitions in the various phases of an electrically induced seizure. The foot switch may be a foot operated momentary switch for placement on a floor, and coupled to the digital controller 44 by a cable, which may be activated by simply pressing down for a short period of time with either foot by the operator. In a preferred embodiment of stimulator 40, user input 42 includes a foot switch (not shown) which may be used to activate the stinulus and thereafter to activate and deactivate timers for recording the duration of seizure phases. For example and not by way of limitation, each pressing of the foot switch may turn off a timer and simultaneously activate another timer allowing the user to simply "mark" the transitions between seizure phases. Electrodes 18 may be coupled to the stimulator 40 with a cable or wiring 20. Furthermore, the electrodes 18 may be Spiegel corneal electrodes.

Figure 3:
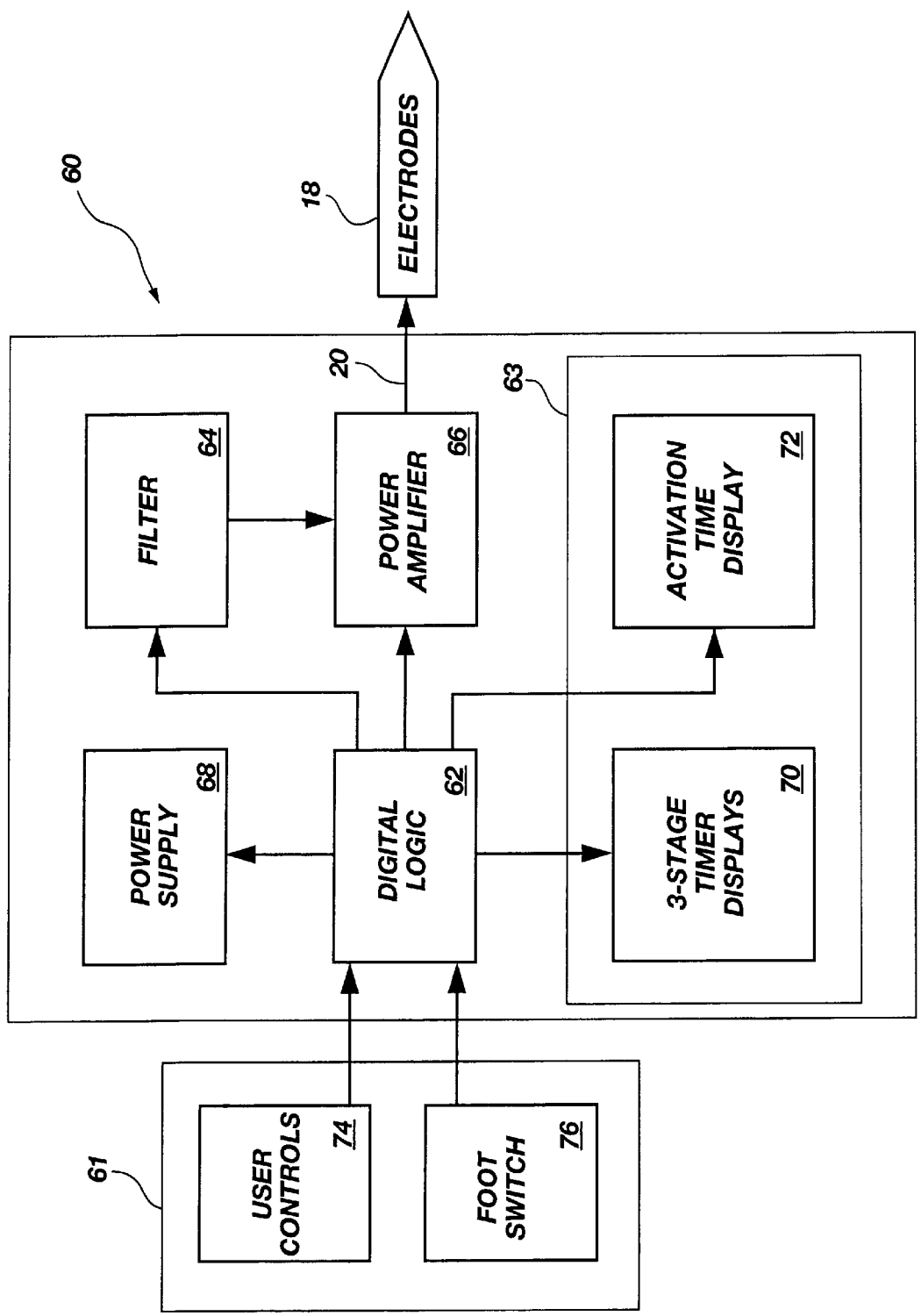
FIG. 3 is a block diagram of yet another embodiment of a stimulator according to this invention.

FIG. 3 illustrates a block diagram of yet another embodiment of a stimulator 60 according to this invention. The stimulator 60 may include digital logic 62, coupled to user input 61, a display 63 coupled to the digital logic 62, a filter circuit 64 coupled to the digital logic 62, a power amplifier 66 coupled to the digital logic 62 and coupled to the filter circuit 64, electrodes 18 coupled to the power amplifier 66, and a power supply 68 to provide power to circuitry contained in the digital logic 62, the filter circuit 64, the power amplifier 66 and the display 63.

Digital logic 62 may include a microprocessor, a microcontroller or other programmable logic device for receiving input signals from user input 61 and providing control signals for filter circuit 64, the power amplifier 66 and the display 63. Digital logic 62 includes at least three timing circuits (not shown) for measuring seizure phases based on input signals received from user input 61. Digital logic 62 provides control signals to filter circuit 64, power amplifier 66 and display 63. Digital logic 62 also provides timing information to be displayed on display 63. Filter circuit 64 converts a low voltage 60 Hertz square wave received from digital logic 62 into a low voltage 60 Hertz sine wave. Power amplifier 66 amplifies the low voltage 60 Hertz sine wave received from the filter circuit 64 generates a sinusoidal stimulus with current ranging from about 2 mA rms to about 250 mA rms and preferably from about 4 mA rms to about 200 mA rms and voltage ranging from about ±180 volts to about ±240 volts, preferably ranging about ±190 volts.

Display 63 may be a cathode ray tube, LCD, gas-plasma display, field effect display, or any other type of visual display for conveying display information to users or observers. Display information may include current settings and/or activation time of stimulus. Display 63 may be integrated into the stimulator 60 or may be a separate component such as a monitor coupled to the stimulator 60 by a video cable or other means well known to a person of skill in the art. Display 63 may be a combination of individual displays grouped together, or apart, for displaying numerical or graphical information. As shown in FIG. 3, display 63 includes three-stage timer displays 70 and activation time display 72. The three-stage timer displays 70 may be used to display elapsed time in three phases of a seizure. The activation time display 72 displays the activation time of the stimulus.

As shown in FIG. 3 user input 61 includes user controls 74 which may be physically integrated with the stimulator 60, or remotely coupled to the stimulator 60, for setting the current and activation time of the stimulus. User controls 74 may include range select buttons, knobs, switches, etc., for adjusting the desired current to be delivered in the stimulus. User input 61 also includes a foot switch 76 configured to allow the user to change the state of operation of the stimulator 10 and enter timing signals corresponding to the transitions in the various phases of an electrically induced seizure. For example, and not by way of limitation, a foot switch 76 may be used to activate the stimulus and thereafter to activate and deactivate timers for recording the duration of seizure phases. Each pressing of the foot switch may turn off a timer and simultaneously activate another timer allowing the user to simply "mark" the transitions between seizure phases. The stimulator 60 may also include electrodes 18 coupled to the stimulator 60 with a cable or wiring 20. The electrodes 18 may be Spiegel corneal electrodes.

Figure 4:
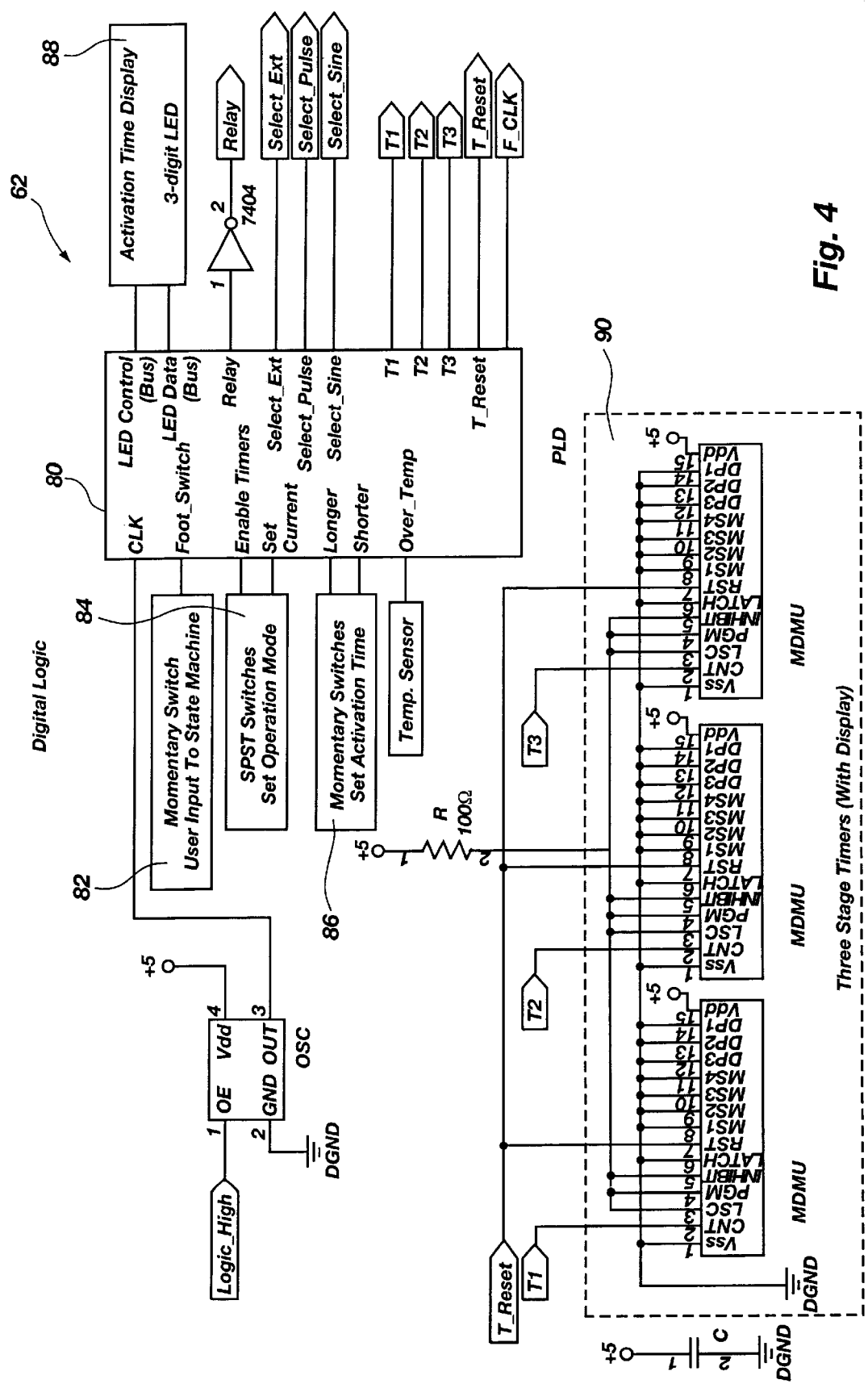
FIG. 4 is a schematic diagram of an embodiment of digital logic according to the embodiment of a stimulator shown in FIG. 3.

FIG. 4 is a schematic diagram of one embodiment of digital logic 62 according to the embodiment of a stimulator shown in FIG. 3. Digital logic 62 includes a programable logic device (PLD) 80 which receives input from a foot switch 82, operational mode switches 84, and activation time set switches 86. Switches 82, 84 and 86 may be included in user controls 74 (see, FIG. 3). The PLD 80 drives activation time display 88 and three stage timers with display 90.

Figure 5:
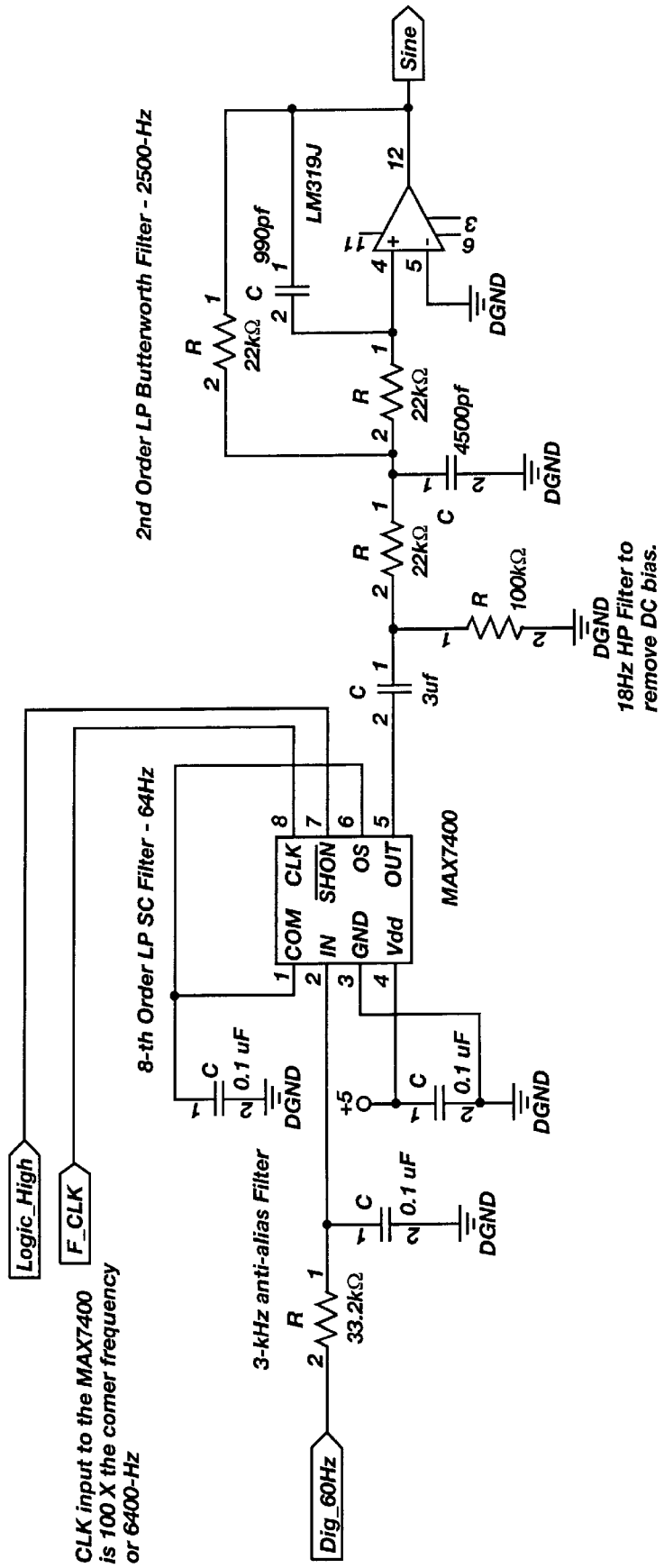
FIG. 5 is a schematic diagram of an embodiment of a filter according to the embodiment of a stimulator shown in FIG. 3.

FIG. 5 is a schematic diagram of one embodiment of a filter circuit 64 according to the embodiment of a stimulator shown in FIG. 3. The filter circuit 64 converts a low voltage 60 Hertz square wave signal to a low voltage 60 Hertz sine wave signal.

Figure 6:
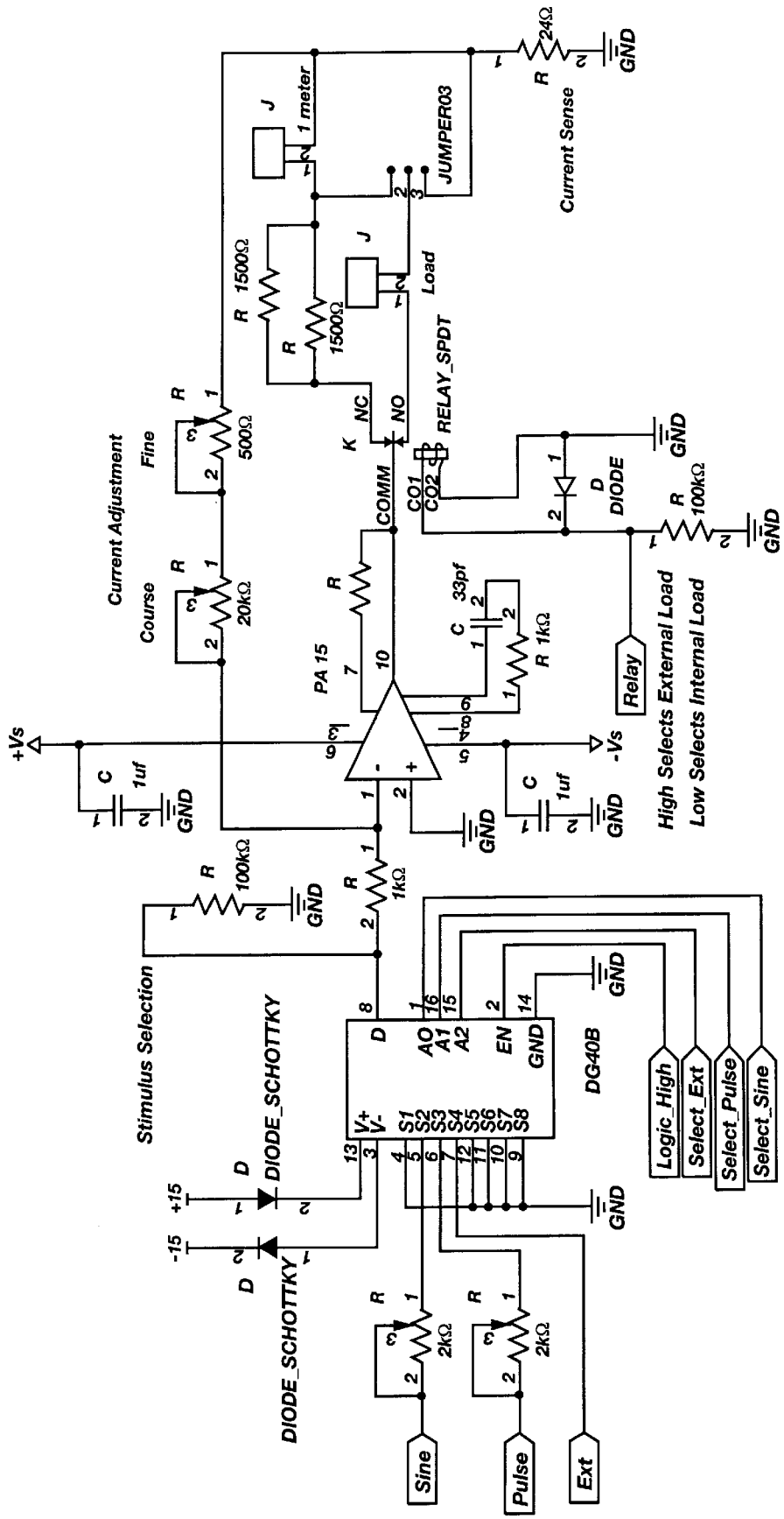
FIG. 6 is a schematic diagram of an embodiment of a power amplifier according to the embodiment of a stimulator shown in FIG. 3.

FIG. 6 is a schematic diagram of an embodiment of a power amplifier 66 according to the embodiment of a stimulator shown in FIG. 3. The power amplifier 66 converts the low voltage 60 Hertz sine wave signal output by the filter circuit 64 and amplifies it to a 60 Hertz stimulus with voltage ranging from about ±190 volts at a current in the range from about 4 mA rms to about 200 mA rms.

Methods of Operation

The preferred method of operating a stimulator according to this invention is as follows. When the stimulator is turned on or reset it begins in an initial state. Once the stimulator is in the initial state, the user may set the desired activation time and current. Either of these settings may be performed after initialization. Alternatively, each setting may be separated by pressing the foot switch to put the stimulator in a current-set mode or activation time set mode. To set the current, the user adjusts a current setting of the stimulator by way of user controls. User controls may include range select buttons, knobs, switches, etc., for adjusting the desired current to be delivered in the stimulus. The current setting may default to a particular setting upon initialization and may also be programable to default to any allowable current setting. To set the activation time, the user may press buttons or adjust knobs, etc. to select the desired duration of the stimulus. The activation may default to a given activation time, e.g., 0.2 seconds, or any other programmable activation time. The order of setting activation time and current are not critical to the invention.

Once the activation time and current are set, the user attaches the electrodes to the test animal. This operation frequently requires the use of both hands of the operator. The operator may then activate the stimulus using the foot switch. The foot switch delivers the electrical stimulus through the electrodes for the duration of the activation time thereafter shutting off and automatically switching on a first timer at the end of the activation time. The user will then observe the test animal during the electrically induced seizure for a transition from a first phase, typically the hindleg flexor component of the tonic phase. As the test animal begins to transition into a second phase, typically the hindleg extensor component of the tonic phase, the user presses the foot switch to mark the transition between the first and the second phase, thereby turning off a first timer circuit and automatically turning on a second timer circuit to measure the second phase. As the test animal begins to transition into a third phase, typically the intermittent, whole-body clonic phase, the user presses the foot switch again to mark the transition between the second phase and the third phase, thereby turning off the second timer and automatically turning on a third timer circuit to measure the duration of the third phase of the electrically induced seizure. As the test animal begins to transition into a fourth phase, typically the muscular relaxation phase, the user presses the foot switch once again to turn off the third timer circuit. The information recorded by the three timer circuits may be displayed realtime on the display and may be stored within the stimulator or sent to a optional computer through a computer interface for further analysis.

As some users of the stimulator disclosed herein will not be interested in timing the various phases of the induced seizure, alternative methods of operation are also contemplated. An alternative method of operation of a stimulator according to the invention includes the above steps of initializing the stimulator, setting activation time and current, delivering the stimulus with the foot switch without activating any timers. Yet another method of operation of a stimulator according to the invention includes the above steps of initializing the stimulator, setting activation time and current, delivering the stimulus with the foot switch and activating only one timer to capture the period of the entire seizure from delivery of the stimulus to the transition into the fourth phase of the seizure with one additional pressing of the foot switch at the appropriate time by the user. Such alternative methods of operation disclosed above may be included in the preferred embodiment of a stimulator according to the invention by means of toggle switches or other user controls.

Figure 7:
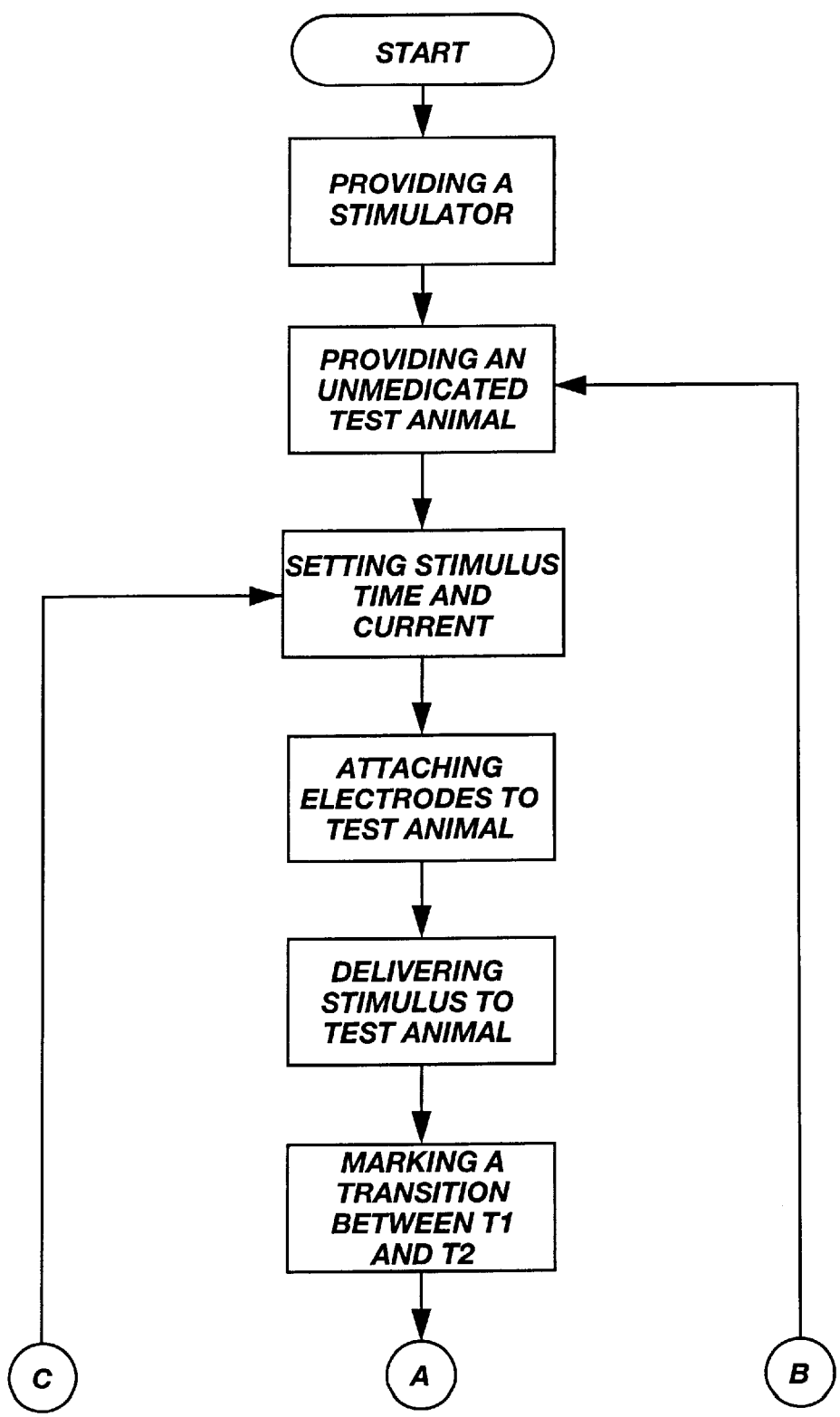
FIGS. 7 and 8 are a flow charts of steps in a method of measuring the phases of an electrically induced seizure in a test animal and a method of analyzing the efficacy of a candidate anticonvulsant drug according to this invention.
Figure 8:
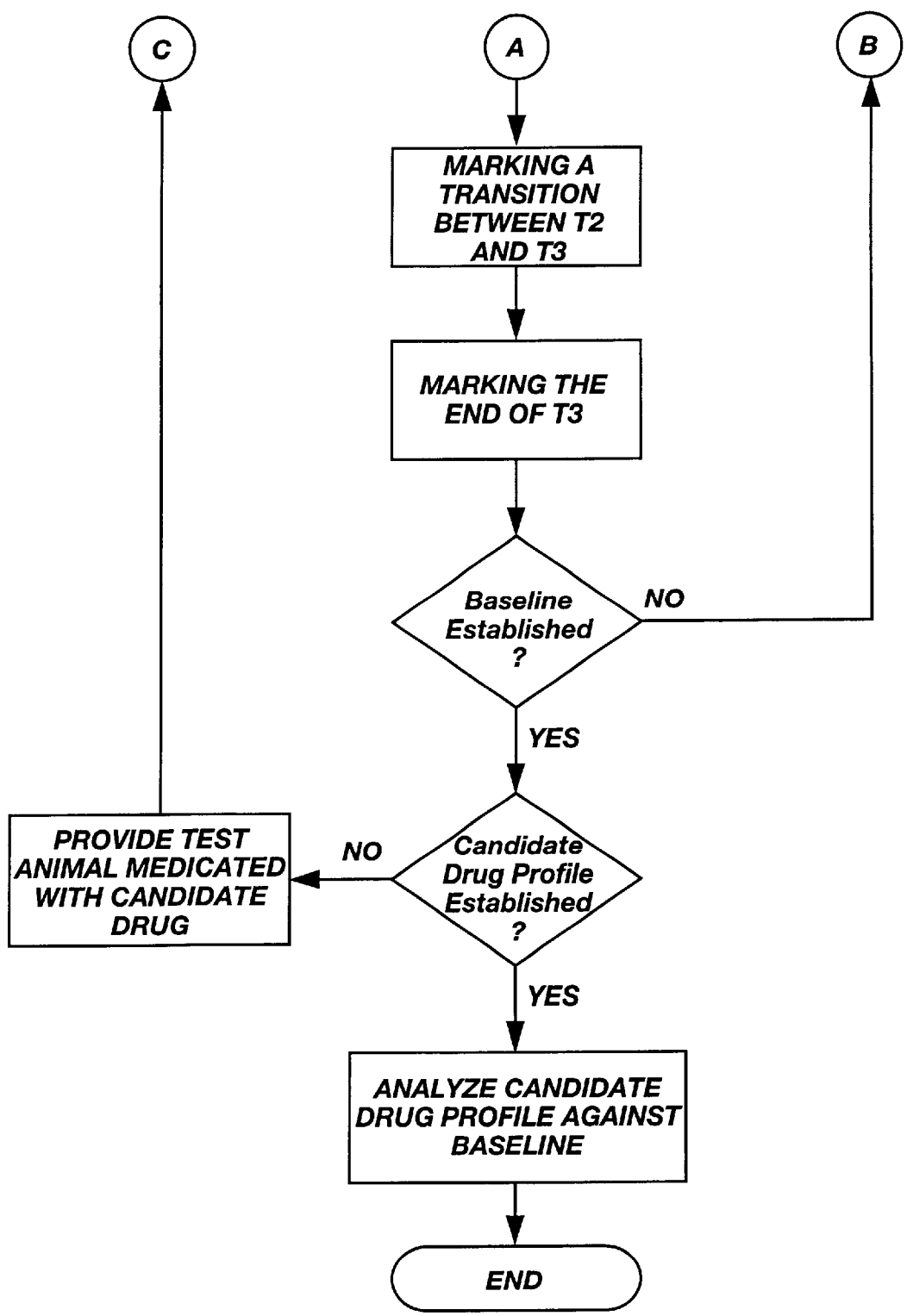

FIGS. 7 and 8 are flow charts disclosing a method of measuring the phases of an electrically induced seizure in a test animal and a method of analyzing the efficacy of a candidate anticonvulsant drug according to this invention. The method of measuring the phases of an electrically induced seizure in a test animal includes: providing an unmedicated test animal, providing a stimulator according to this invention as disclosed above, setting a stimulus time and current, attaching said electrodes to the test animal, delivering the stimulus to the test animal to induce a seizure and beginning a first timer at the end of stimulus delivery, marking a transition between a first phase of the seizure and a second phase of the seizure, marking a transition between the second phase of the seizure and a third phase of the seizure, marking the end of the third phase of the seizure. The marking steps may be accomplished using a foot switch.

The method of analyzing the efficacy of a candidate anticonvulsant drug according to the invention includes the aforementioned steps as described in the method of measuring the phases of an electrically induced seizure in a test animal and the additional following steps: repeating the above steps a statistically sufficient number of times to establish a baseline for each phase of a seizure, repeating the above steps a statistically sufficient number of times with a test animal medicated with a candidate anticonvulsant drug to establish a candidate drug profile, and analyzing the candidate drug profile against the baseline for reduction in seizure phase duration. A "statistically sufficient number of times" may be determined by any conventional means known to one of skill in the art of statistics. Establishing a baseline and a candidate drug profile may be performed by any manner known to one of skill in the art.

Although the invention has been described with reference to particular embodiments, the invention is not limited to these described embodiments. Rather, it should be understood that the embodiments described herein are merely exemplary and that a person skilled in the art may make many variations and modifications without departing from the spirit and scope of the invention. For example, a person skilled in the art may combine any of the features illustrated or described in a given embodiment above in another embodiment which may not have such a feature illustrated or described. It would also be within the scope of the invention to integrate two or more components described herein into a single component performing all of the functions of the original two or more components. All such variations and modifications are intended to be included within the scope of the invention as defined in the appended claims.

What is claimed is:

1. A stimulator, comprising:

stimulus generation and control circuitry for providing an electrical stimulus sufficient to induce an epileptic seizure in a laboratory test animal;

a display, coupled to said stimulus generation and control circuitry, for displaying three phases of the electrically induced epileptic seizure; and a user input device, coupled to said stimulus generation and control circuitry, configured for a user to control delivery of the electrical stimulus and enter epileptic seizure phase transition timing signals.

2. The stimulator of claim 1, wherein said stimulus generation and control circuitry comprises:

a power supply for providing a periodic source signal;

digital logic circuitry coupled to said power supply and said user input device for receiving selected parameters of said electrical stimulus;

a filter circuit coupled to said power supply and said digital logic circuitry for shaping said periodic source signal; and a power amplifier coupled to said power supply, said digital logic circuitry and said filter circuit for receiving said shaped periodic source signal from said filter circuit and generating said electrical stimulus according to said selected parameters.

3. The stimulator of claim 1, wherein said display comprises:

a first timer for displaying elapsed time corresponding to a first phase of an epileptic seizure;

a second timer for displaying elapsed time corresponding to a second phase of an epileptic seizure; and a third timer for displaying elapsed time corresponding to a third phase of an epileptic seizure.

4. The stimulator of claim 3, wherein said display further includes:

an activation time display for displaying the total duration time for said electrical stimulus.

5. The stimulator of claim 1, wherein said user input device includes a foot switch configured for selectively changing a state of operation of said stimulator.

6. The stimulator of claim 1, wherein said user input device includes controls for adjusting current delivered by said electrical stimulus and adjusting activation time of said electrical stimulus.

7. The stimulator of claim 1, further comprising a stimulus cable and electrodes for delivering said electrical stimulus to a test animal.

8. The stimulator of claim 7, wherein said electrodes are Spiegel electrodes.

9. A stimulator configured for inducing a maximal seizure in a test animal comprising:

a digital controller for controlling operations of the stimulator;

a stimulus generator coupled to said digital controller for providing a stimulus sufficient to induce a maximal seizure in a test animal; and a display coupled to said digital controller configured for displaying operational status of said stimulator and seizure phase duration.

10. The stimulator of claim 9, wherein said digital controller includes at least three timer circuits.

11. The stimulator of claim 9, wherein said stimulus generator includes:

a filter coupled to said digital controller for converting a square wave input to a sine wave output; and a power amplifier coupled to said digital controller and receiving said sine wave from said filter for amplifying the peak-to-peak voltage of said sine wave producing a stimulus.

12. The stimulator of claim 11, wherein said stimulus is approximately 60 Hz, with voltage ranging from about ±240 volts, and current ranging between about 2 mA rms to about 250 mA rms.

13. The stimulator of claim 9, wherein said display includes at least three timer displays.

14. The stimulator of claim 13, wherein said display further includes an activation time display.

15. The stimulator of claim 9, further comprising a user input device for inputting timing events.

16. The stimulator of claim 15, wherein said user input device is a foot switch configured for operation by a user of said stimulator to mark transitions between phases of a seizure.

17. The stimulator of claim 9, further including an interface to a computer coupled to said digital controller for uploading timing and stimulus information for analysis.

18. A method of measuring phases of an electrically induced seizure in a test animal, comprising:

providing a stimulator capable of electrically inducing a seizure, including:
a stimulus generator for providing a stimulus;
three timers, T1, T2 and T3 coupled to said stimulus generator for measuring seizure phase duration;
a user input device coupled to said three timers for starting and stopping each of said three timers;
controls coupled to said stimulus generator for selecting current and duration of said stimulus; and
electrodes coupled to said stimulus generator configured for attachment to said test animal for delivering said stimulus;

providing a test animal;

setting a stimulus time and current using said controls;

attaching said electrodes to said test animal;

delivering said stimulus to said test animal inducing a seizure in accordance with said set stimulus time and said current marking a transition between a first phase of said seizure and a second phase of said seizure using said user input device;

marking a transition between said second phase of said seizure and a third phase of said seizure using said user input device; and marking the end of said third phase of said seizure.

19. The method of claim 18, wherein said test animal has been medicated with a candidate anticonvulsant drug.

20. A method of analyzing the efficacy of a candidate anticonvulsant drug by measuring phases of an electrically induced seizure in a test animal, comprising:

(a) providing a stimulator capable of electrically inducing a seizure, including:
a stimulus generator for providing a stimulus;
three timers, T1, T2 and T3 coupled to said stimulus generator for measuring duration of three seizure phases;

a user input device coupled to said three timers for starting and stopping each of said three timers;

controls coupled to said stimulus generator for selecting current and duration of said stimulus; and electrodes coupled to said stimulus generator configured for attachment to said test animal for delivering said stimulus;

(b) providing an unmedicated test animal;

(c) setting a stimulus time and current using said controls;

(d) attaching said electrodes to said test animal;

(e) delivering said stimulus to said test animal inducing a seizure in accordance with said set stimulus time and said current (f) marking a transition between a first phase of said seizure and a second phase of said seizure using said user input device;

(g) marking a transition between said second phase of said seizure and a third phase of said seizure using said user input device;

(h) marking the end of said third phase of said seizure;

(i) repeating steps (b) through (h) a statistically sufficient number of times to establish a baseline for each phase of a seizure;

(j) providing a test animal medicated with a candidate anticonvulsant drug and repeating steps (c) through (h) for a statistically sufficient number of times to establish a candidate drug profile; and (k) analyzing said candidate drug profile against said baseline for reduction in seizure phase length.

21. The method of claim 20, wherein said user input device includes a foot switch.

* * * * *